United States Patent [19]

Lyons et al.

[11] 4,237,309

[45] * Dec. 2, 1980

[54] METHOD FOR THE PREPARATION OF PHENOLIC ACETATES AND PARAFORMALDEHYDE

[75] Inventors: James E. Lyons, Wallingford; George Suld, Springfield; Robert W. Shinn, Aston, all of Pa.

[73] Assignee: Suntech, Inc., Philadelphia, Pa.

[*] Notice: The portion of the term of this patent subsequent to Dec. 2, 1997, has been disclaimed.

[21] Appl. No.: 957,612

[22] Filed: Nov. 3, 1978

[51] Int. Cl.³ .................. C07C 67/39; C07C 69/157
[52] U.S. Cl. ................................ 560/131; 568/470
[58] Field of Search ........................................ 560/131

[56] References Cited

U.S. PATENT DOCUMENTS

| 3,772,383 | 11/1973 | Kominami et al. | 560/131 |
| 4,056,572 | 11/1977 | Bashkirov et al. | 560/131 |

OTHER PUBLICATIONS

Grozhan et al., Doklady Akad. Nauk. SSSR, 204, (4), pp. 872–873, (1972).

*Primary Examiner*—Jane S. Myers
*Attorney, Agent, or Firm*—J. Edward Hess; Donald R. Johnson; Stanford M. Back

[57] ABSTRACT

The oxidation of methyl benzenes with air or oxygen in the presence of acetic anhydride, benzaldehyde and an acid catalyst under mild reaction conditions yields a phenolic acetate and formaldehyde or paraformaldehyde when the ratio of acetic anhydride to methyl benzene is adjusted to provide the selective formation of the phenolic acetate and formaldehyde or paraformaldehyde. In this process, it is essential that the flow of air or oxygen through the reaction medium be maintained at a sufficient rate to provide for the continuous removal of formaldehyde as it is formed. The formaldehyde may then be recovered in the form of paraformaldehyde.

9 Claims, No Drawings

METHOD FOR THE PREPARATION OF PHENOLIC ACETATES AND PARAFORMALDEHYDE

BACKGROUND OF THE INVENTION

This invention relates to a process for the preparation of a phenolic acetate and paraformaldehyde. More particularly, it relates to a novel process for the oxidation of a methyl benzene under controlled conditions which selectively provides for the formation of said phenolic acetate and formaldehyde or paraformaldehyde.

In copending application Ser. No. 957,614, by Suld et al., which is incorporated here by reference, there is disclosed the novel finding that the oxidation of methyl benzenes, such as toluene, with air or oxygen in the presence of acetic anhydride and an acid catalyst to form a phenolic acetate and methylene diacetate may be carried out under mild reaction conditions when small amounts of benzaldehyde are added to the reaction. The resulting acetates may then be pyrolyzed to yield phenolic compounds and formaldehyde, respectively. This was in contrast to still earlier work, by Lyons et al., Ser. No. 945,747, carried out at high temperatures and pressures. The oxidation product, in both cases, was a phenolic acetate and methylene diacetate. Also, in both cases, it was taught that the methylene diacetate could then be converted to formaldehyde in a separate step by pyrolysis.

SUMMARY OF THE INVENTION

It has now been found, in accordance with the present invention, that quite surprisingly, paraformaldehyde, together with a phenolic acetate, may be formed directly, and under mild conditions, by the oxidation of methyl benzenes in the presence of acetic anhydride, benzaldehyde, and an acid catalyst when (1) the ratio of acetic anhydride to methyl benzene is controlled in such a fashion as to induce the selective formation of formaldehyde and the phenolic acetate, to the exclusion of methylene diacetate formation; and (2) the flow rate of air or oxygen through the reaction medium is sufficient to remove formaldehyde as it is formed.

DESCRIPTION OF THE INVENTION

The process, using the oxidation of toluene as an example, may be illustrated by the following equation:

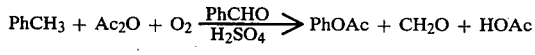

This reaction scheme is in contrast to that of the above-mentioned copending application Ser. No. 957,614 which reads as follows:

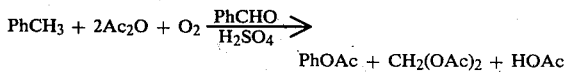

Thus it will be seen that by reducing the amount of acetic anhydride in the present case there is unexpectedly and selectively formed in addition to phenyl acetate, formaldehyde, to the substantial exclusion of methylene diacetate. When this modification is accompanied by an adequate, continuous flow of air or oxygen, formaldehyde vapors come out of solution where they are condensed and recovered from the reaction medium, together with acetic acid and lesser amounts of certain methyl benzene-derived by products. As aforestated, the phenyl acetate may then be pyrolyzed to form phenol.

It will be understood, of course, that this novel method is equally applicable to other methyl benzene compounds such as xylenes and trimethyl benzenes, e.g., mesitylene and pseudocumene.

In general, the process is carried out by oxidizing the desired methyl benzene with air or oxygen in the liquid phase at pressures of at least 1 atmosphere and at temperatures as low as 80°C. to form a phenolic acetate and paraformaldehyde, together with the aforementioned acetic acid and methyl benzene-derived by-products. After separation and recovery of the phenyl acetate and paraformaldehyde, the acetic acid may be routinely converted to acetic anhydride and recycled to the oxidation step.

In order to fully achieve the objects of this invention and optimize the formation of paraformaldehyde, it is essential that acetic anhydride be metered into the reaction mixture at a rate such that there is sufficient acetic anhydride present to selectively react with one of the toluene oxidation products, (phenol) to give phenyl acetate but not enough acetic anhydride to convert the other oxidation product (formaldehyde) to methylene diacetate, under reaction conditions. This may conveniently be accomplished by careful control of the amount of acetic anhydride introduced into the reaction as the oxidation process is monitored, e.g., by conventional chromatographic techniques.

The amounts and flow rate of air or oxygen are not critical but should in any event be sufficient to both oxidize the methyl benzene and at the same time remove the formaldehyde as it is formed. Thus, it is only essential that the air or oxygen be provided in a continuous flow. Generally, however, it may be said that the amount of said gas can vary from about 1 to 100 volumes of gas per volume of liquid reaction mixture per unit of time, and preferably should be about 10 volumes of gas per minute per volume of reaction mixture.

The reaction is carried out in the presence of an acid catalyst, preferably $H_2SO_4$, and benzaldehyde. The weight ratio of $H_2SO_4$ to methyl benzene should generally be from about $5 \times 10^{-4}$ to $1 \times 10^{-2}$, and preferably $1 \times 10^{-3}$ to $5 \times 10^{-3}$, while the amount of benzaldehyde employed should be about 0.01 to 1.0 moles, and preferably 0.05 to 0.10 moles, per mole of alkyl benzene.

If desired, the reaction may be run in excess methyl benzene reactant as a solvent, or in a suitable organic solvent such as benzene, chlorobenzene, or acetic acid. The latter is preferred inasmuch as increased selectivities are observed. In order for rapid reactions in acetic acid, promoters such as Caro's Dry Acid should be present in amounts of 10–100 wt. % based on the amount of acetic anhydride used.

The formaldehyde may be recovered either as a monomer or preferably as a solid polymer, paraformaldehyde, which solidifies on a cool surface downstream of the reactor.

The reaction mixture containing the phenolic acetate, as well as lesser amounts of acetic acid, methyl benzene derived by-products, and the like is routinely treated to remove the acid catalyst, following which the acetate may be recovered by distillation under vacuum.

The recovered phenolic acetate is then converted to phenol, cresol or the like by pyrolysis. This is conventionally achieved by heating the acetate at temperatures of from about 500° to 1000° C., preferably at about 625° C., and preferably in the presence of a catalyst such as trimethyl phosphate, and recovering the desired product by routine means.

The recovered acetic acid may then be converted to acetic anhydride for recycling to the initial oxidation step. This may readily be achieved e.g., by contacting ketene with acetic acid at room temperature in the liquid phase.

The following examples are provided solely for purposes of illustrating but not limiting the novel process of this invention.

EXAMPLE 1

Into a manometric gas-recirculation oxidation apparatus was charged:

| | |
|---|---|
| Toluene | 42.8 ml |
| Acetic Anhydride | 1.0 ml |
| Benzaldehyde | 1.0 ml |
| Sulfuric Acid | 2 drops (~0.06 g) |

Air in the reaction flask was replaced by nitrogen and the reaction mixture was heated to ~100° C. When the temperature reached 100° C. nitrogen was replaced by pure oxygen and the gas recirculating pump was started, sparging oxygen through the liquid at 300–400 ml/min. The gas uptake was recorded with time by measuring the displacement in a mercury filled gas buret assembly. Liquid samples were withdrawn from the reaction flask and analyzed by standard gas chromatographic techniques. Acetic anhydride was added, incrementally, to the reaction mixture from a motor driven syringe pump between 49–108 min., 0.72 ml and 172–220 min. 0.20 ml. At the end of this time period (3 hours, 40 min.) the oxygen uptake was 349 ml and the oxidized product contained phenyl acetate (PA) 26%, methylene diacetate (MDA) 7%, phenyl hemiformal acetate (PHF) 2%, benzyl acetate (BAC) 14%. A substantial quantity of a white solid covered the cold surfaces of the reactor and condenser. Analysis showed this material to be a solid polymer of formaldehyde, i.e., paraformaldehyde.

In accordance with foregoing procedure, but substituting xylene for toluene, there is obtained cresyl acetate and paraformaldehyde, together with acetic acid and related by-products.

EXAMPLE 2

Into the reactor was charged:

| | |
|---|---|
| Toluene | 42.8 ml |
| Acetic Anhydride | 1.0 ml |
| Benzaldehyde | 1.0 ml |
| Potassium persulfate | 0.54 g |
| Sulfuric Acid | 2 drops (~0.06 g) |

The reaction was carried out as in Example 1, at 100° C. with incremental addition of acetic anhydride between 33–73 min., 0.82 ml and 100–160 min., 0.62 ml. After 2 hrs. 40 min. the reaction was stopped, with a total oxygen uptake of 280 ml. The oxidation product contained PA-17%, MDA-trace, BAC 8%. The cold walls of the reactor and condenser were covered with a white solid which was shown to be solid paraformaldehyde by infrared analysis.

EXAMPLE 3

Into the reactor was charged:

| | |
|---|---|
| Toluene | 42.8 ml |
| Acetic Anhydride | 16.0 ml |
| Benzaldehyde | 1.0 ml |
| Potassium Persulfate | 0.43 g |
| Sulfuric Acid | 2 drops (~0.06 g) |

The reaction was carried out as in Example 1, except that all the reactants were present initially and no incremental addition was carried out. At the end of 5 hr. reaction had stopped with total of 240 ml oxygen absorbed.

Only 3% PA and MDA were found among the oxidation products which also contained 19% BAC. No solid paraformaldehyde was detected.

The invention claimed is:

1. A process for the oxidation of methyl benzenes to form a phenolic acetate and formaldehyde or paraformaldehyde which comprises reacting said methyl benzene with air or oxygen and acetic anhydride in the presence of an acid catalyst and benzaldehyde, in amounts of from about 0.01–1.0 moles based on the methyl benzene, at temperatures of from about 80° C. to 150° C. and pressures of at least about 1 atmosphere, wherein the amount of acetic anhydride present is insufficient to form methylene diacetate, thereby selectively forming said phenolic acetate, together with free formaldehyde or paraformaldehyde, and wherein the flow rate of air or oxygen is sufficient to provide the continuous removal of said formaldehyde or paraformaldehyde as it is formed.

2. The process of claim 1 wherein the acid catalyst is $H_2SO_4$.

3. The process of claim 1 wherein the pressure is from about 1 to 10 atmospheres.

4. The process of claim 1 wherein a suitable organic solvent is employed.

5. The process of claim 4 wherein the solvent is acetic acid in the presence of a promoter.

6. The process of claim 5 wherein the reaction is carried out in the presence of a persulfate promoter.

7. The process of claim 6 wherein the promoter is Dry Caro's acid.

8. The process of claim 1 wherein the methyl benzene is toluene and the products are phenyl acetate and formaldehyde and/or paraformaldehyde.

9. The process of claim 1 wherein the methyl benzene is xylene and the products are cresyl acetate and formaldehyde and/or paraformaldehyde.

* * * * *